US 8,038,694 B2

(12) United States Patent
Takemoto et al.

(10) Patent No.: US 8,038,694 B2
(45) Date of Patent: Oct. 18, 2011

(54) LANCET INSTRUMENT

(75) Inventors: Masafumi Takemoto, Nakakoma-gun (JP); Hirofumi Yazaki, Nakakoma-gun (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 385 days.

(21) Appl. No.: 11/661,594

(22) PCT Filed: Sep. 6, 2005

(86) PCT No.: PCT/JP2005/016337
§ 371 (c)(1),
(2), (4) Date: Mar. 1, 2007

(87) PCT Pub. No.: WO2006/028096
PCT Pub. Date: Mar. 16, 2006

(65) Prior Publication Data
US 2008/0103517 A1    May 1, 2008

(30) Foreign Application Priority Data

Sep. 6, 2004  (JP) ................................. 2004-258943

(51) Int. Cl.
*A61B 17/32* (2006.01)
(52) U.S. Cl. ...................................................... 606/181
(58) Field of Classification Search .................. 600/573, 600/578, 583, 584; 604/136; 606/181, 182, 606/183
See application file for complete search history.

(56) References Cited

U.S. PATENT DOCUMENTS
4,421,123 A * 12/1983 Percarpio ...................... 600/579
(Continued)

FOREIGN PATENT DOCUMENTS
JP    6-133955 A    5/1994
(Continued)

OTHER PUBLICATIONS
International Search Report dated Nov. 10, 2005.
(Continued)

*Primary Examiner* — Gary Jackson
*Assistant Examiner* — David Eastwood
(74) *Attorney, Agent, or Firm* — Buchanan Ingersoll & Rooney PC

(57) ABSTRACT

A lancet instrument detachably fitted to a lancing apparatus, comprising a lancet having a lancet body with a sharp lancet tip at its tip, a lancet hub fixed to the lancet body so that the lancet tip is exposed, and an elastic deformation part extended from the lancet hub in the tip direction and elastically deformable so that the distance thereof from the lancet body can be changed, a ring-like member fitted to the outer periphery of the elastic deformation part and releasable in the tip direction by changing the distance between the elastic deformation part and the lancet body, and a casing having a ring-like member contact part storing the lancet so as to be movable in the longitudinal direction and formed in the inner peripheral part thereof so that the ring-like member is brought into contact therewith and stopped to move in the tip direction and a tip opening through which the lancet tip can be projected. The lancet instrument thus obtained is so formed that the projection of the lancet tip through the tip opening of the casing is blocked by moving the ring-like member released from the elastic deformation part in the tip direction between the tip of the elastic deformation part and the ring-like member contact part to restrict the movement of the lancet.

21 Claims, 9 Drawing Sheets

U.S. PATENT DOCUMENTS

| | | | |
|---|---|---|---|
| 5,314,442 A * | 5/1994 | Morita | 606/182 |
| 5,318,584 A * | 6/1994 | Lange et al. | 606/182 |
| 5,324,303 A | 6/1994 | Strong et al. | |
| 5,454,828 A * | 10/1995 | Schraga | 606/181 |
| 6,540,762 B1 | 4/2003 | Bertling | |
| 2001/0027326 A1* | 10/2001 | Schraga | 606/182 |
| 2001/0039387 A1* | 11/2001 | Rutynowski et al. | 600/573 |
| 2002/0040230 A1* | 4/2002 | Kuhr et al. | 606/181 |
| 2002/0087180 A1* | 7/2002 | Searle et al. | 606/181 |
| 2002/0169470 A1* | 11/2002 | Kuhr et al. | 606/182 |
| 2003/0158568 A1* | 8/2003 | Marshall et al. | 606/181 |
| 2004/0243165 A1 | 12/2004 | Koike et al. | |

FOREIGN PATENT DOCUMENTS

JP    2004-113580 A    4/2004

OTHER PUBLICATIONS

Extended European Search Report issued in corresponding EP 05 78 2218, Jan. 8, 2008, EPO, Berlin, DE.

* cited by examiner

LANCET INSTRUMENT

TECHNICAL FIELD

The present invention relates to a lancet instrument.

BACKGROUND ART

In recent years, accompanying the increase in the number of diabetics, the self monitoring of blood glucose monitoring daily movements in blood sugar level by the patient himself has come to be recommended.

The measurement of blood sugar level is carried out by use of a blood glucose monitoring apparatus for automatically measuring the amount of glucose in blood. Prior to the measurement, the patient must sample his own blood.

A method of sampling blood includes the steps of puncturing the skin of a fingertip by a lancet and then pressing the vicinity of the puncture portion with fingers or the like to squeeze out the blood.

The puncture of a fingertip with a lancet is conducted by use of a lancet instrument (refer to, for example, U.S. Pat. No. 6,540,762) having a lancet and a casing (cap) storing the lancet movably therein. Specifically, the lancet instrument is fitted to the lancing apparatus, and the lancing apparatus is operated to project the lancet, thereby puncturing a fingertip.

In addition, after the puncture (after the use), the lancet instrument in the condition where the lancet tip is located in the casing has the lancet and the casing engaged with each other by friction between the outer periphery of a hub (lancet hub) provided on the lancet and the inner periphery of the casing. This ensures that the lancet tip, after the puncture, can be prevented from projecting through the opening (tip opening) of the casing.

However, in the lancet instrument thus configured, the engagement between the lancet and the casing may be weakened (due to a decrease of the frictional force) due, for example, to vibration or the like, and the lancet may be moved (displaced) toward the opening side, i.e., the lancet tip may project from the opening.

Besides, in the case where the lancet tip of the lancet instrument after the puncture (after the use) projects from the opening, the patient's skin or the like, for example, may be injured by mistake.

DISCLOSURE OF INVENTION

It is an object of the present invention to provide a lancet instrument wherein the projection of a lancet tip through a tip opening after puncture can be securely prevented.

In order to attain the above object, according to the present invention, there is provided a lancet instrument adapted to be detachably fitted to a lancing apparatus when used, includes: a lancet having a lancet body with a sharp lancet tip at its tip, a lancet hub fixed to the lancet body so that the lancet tip is exposed, and an elastic deformation part extended from the lancet hub and elastically deformable so that the distance thereof from the lancet body can be changed; a ring-like member fitted to an outer periphery of the elastic deformation part and releasable in a tip direction by changing the distance between the elastic deformation part and the lancet body; and a casing having a ring-like member contact part storing the lancet so as to be movable in the longitudinal direction and formed in an inner peripheral part thereof so that the ring-like member is brought into contact therewith and blocked to move in the tip direction, and a tip opening through which the lancet tip can be projected, wherein the projection of the lancet tip through the tip opening of the casing is blocked by moving the ring-like member released from the elastic deformation part in the tip direction between the tip of the elastic deformation part and the ring-like member contact part so as to restrict the movement of the lancet.

This makes it possible to securely prevent the lancet tip from projecting through the tip opening after puncture.

Besides, in the lancet instrument according to the present invention, preferably, an inner periphery of the ring-like member has a tapered shape such that the inside diameter of the ring-like member gradually increases in the tip direction, and an outer periphery of a fitting part of the elastic deformation part, to which said ring-like member is fitted, has a tapered shape such that an outside diameter of the fitting part gradually increases in the tip direction.

This ensures that, when the ring-like member is released from the elastic deformation part, the outside diameter on the tip side of the elastic deformation part becomes larger than the inside diameter on the base end side of the ring-like member, so that the ring-like member can be prevented from being again fitted to the elastic deformation part.

In addition, in the lancet instrument according to the present invention, preferably, the taper angle of the inner periphery of the ring-like member is in the range of 1 to 45 degrees.

This ensures easier release of the ring-like member from the elastic deformation part, and makes it possible to assuredly prevent the released ring-like member from being again fitted to the elastic deformation part.

Besides, in the lancet instrument according to the present invention, preferably, the ring-like member is irreversibly released from the elastic deformation part.

This ensures that the ring-like member released from the elastic deformation part would not be again fitted to the elastic deformation part and that the tip of the elastic deformation part is assuredly brought into contact with the base end face of the ring-like member. Therefore, the movement of the lancet in the tip direction is restricted (limited), so that the projection of the lancet tip through the tip opening after the puncture can be prevented more securely.

In addition, in the lancet instrument according to the present invention, preferably, the elastic deformation part includes a plurality of projected parts spaced from each other.

This permits easy elastic deformation of the elastic deformation part.

Besides, in the lancet instrument according to the present invention, preferably, the casing is provided at an inner peripheral part thereof with a lock part inhibiting the movement of the ring-like member in a base end direction, and the ring-like member fitted to the elastic deformation part is brought into contact with the lock part and released from the elastic deformation part by moving the lancet in the base end direction relative to the casing.

This ensures that, at the time of detaching the lancet instrument from the lancing apparatus, the movement of the ring-like member in the base end direction is inhibited, so that the ring-like member can be assuredly released from the lancet (elastic deformation part) pulled in the base end direction together with the lancing apparatus.

In addition, in the lancet instrument according to the present invention, preferably, the casing is provided at an inner peripheral part thereof with a hub engaging part for engagement with an outer peripheral part of the lancet hub, and the force for releasing the lancet hub from the hub engaging part is greater than the force for releasing the ring-like member from the elastic deformation part.

This ensures that the ring-like member can be assuredly released from the elastic deformation part before the lancet (lancet hub) is released from the casing (hub engaging part).

BEST MODE FOR CARRYING OUT THE INVENTION

Now, the lancet instrument according to the present invention will be described in detail below, based on preferred embodiments thereof shown in the accompanying drawings.

First Embodiment

Figure 4:
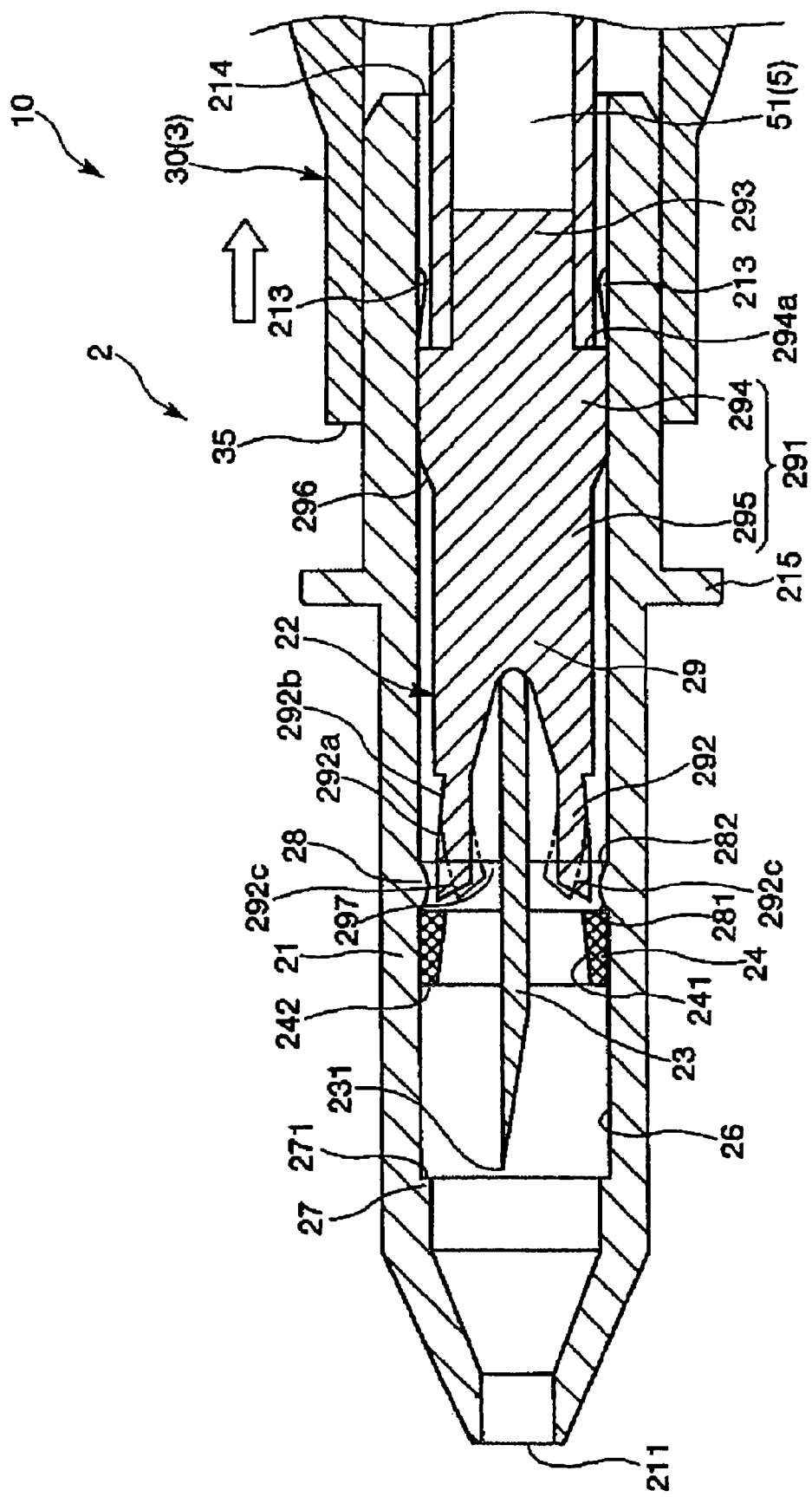
FIG. 4 is a longitudinal sectional view showing the first embodiment
Figure 5:
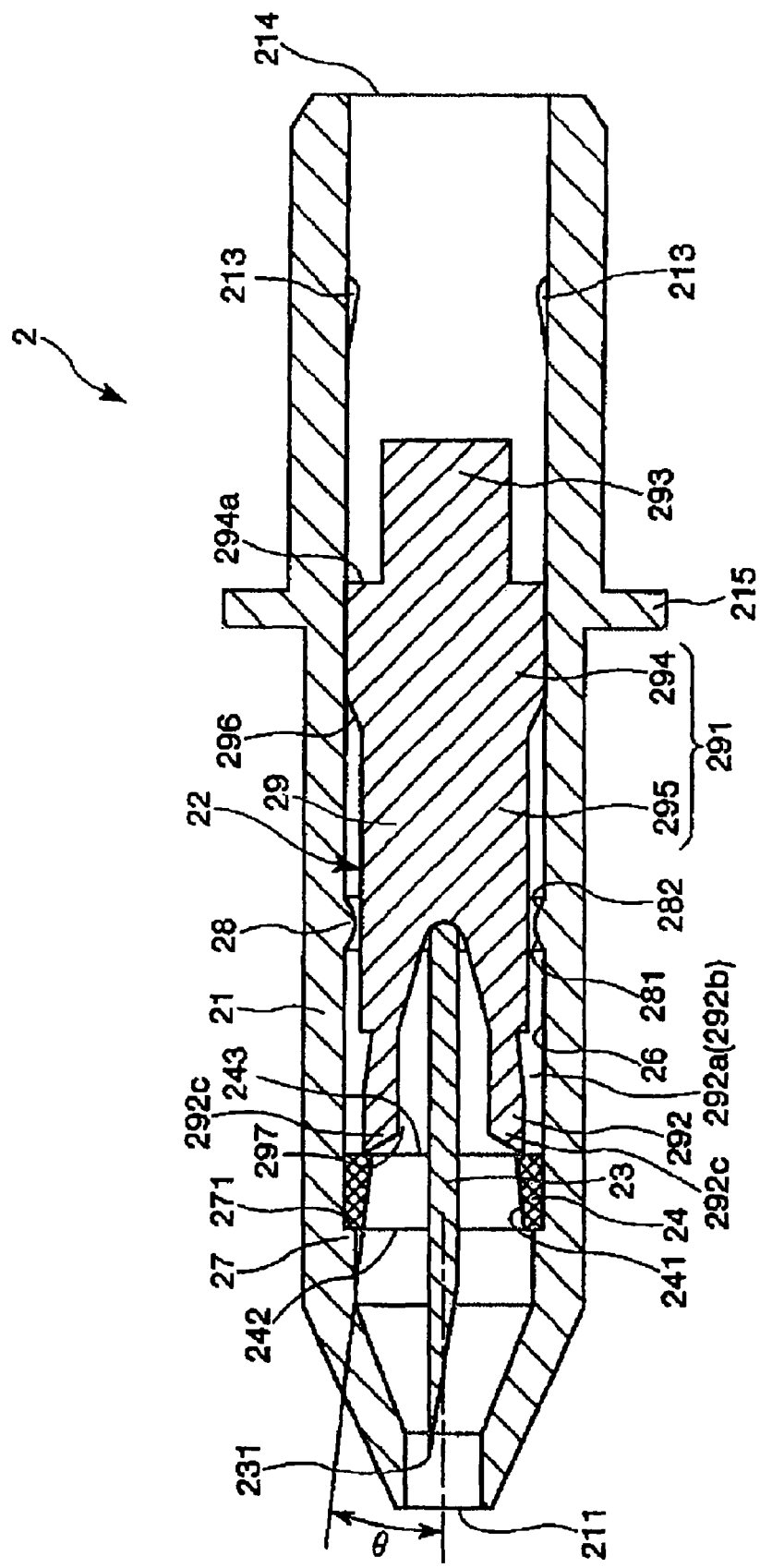
FIG. 5 is a longitudinal sectional view showing the first embodiment (in a third condition) of the lancet instrument according to the invention.
Figure 6:
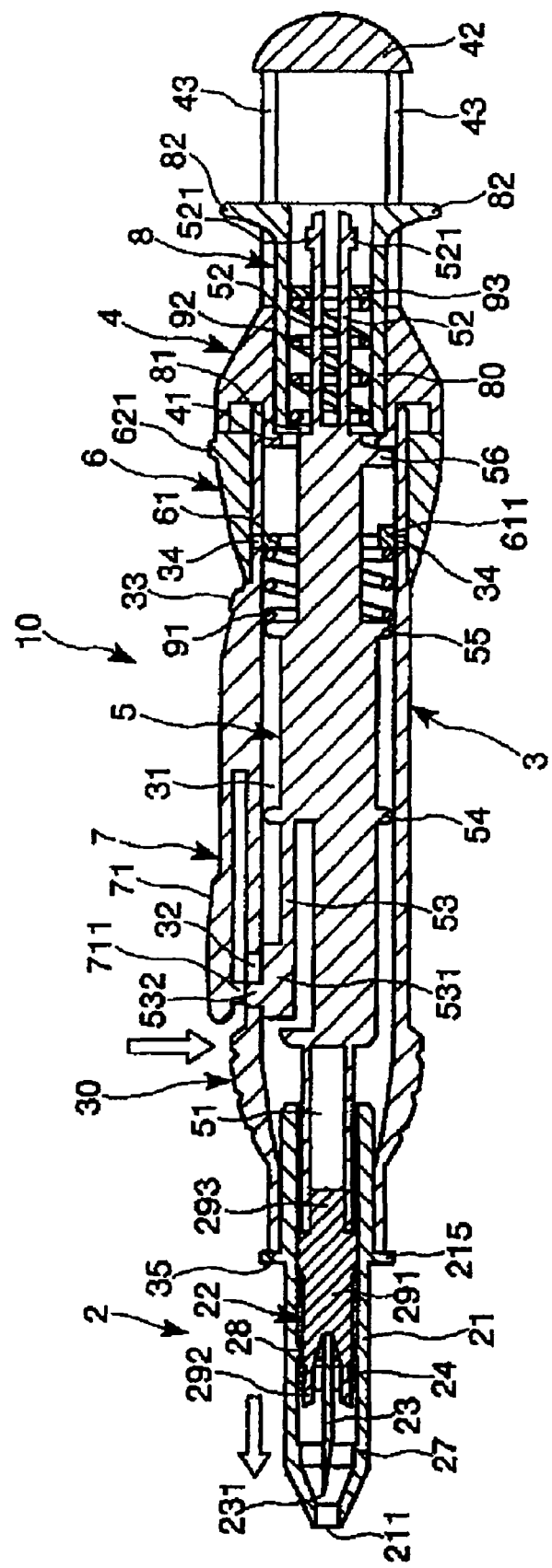
FIG. 6 is a view (longitudinal sectional view) for illustrating the method of using the lancet instrument (first embodiment) according to the invention by fitting it to a lancing apparatus.
Figure 7:
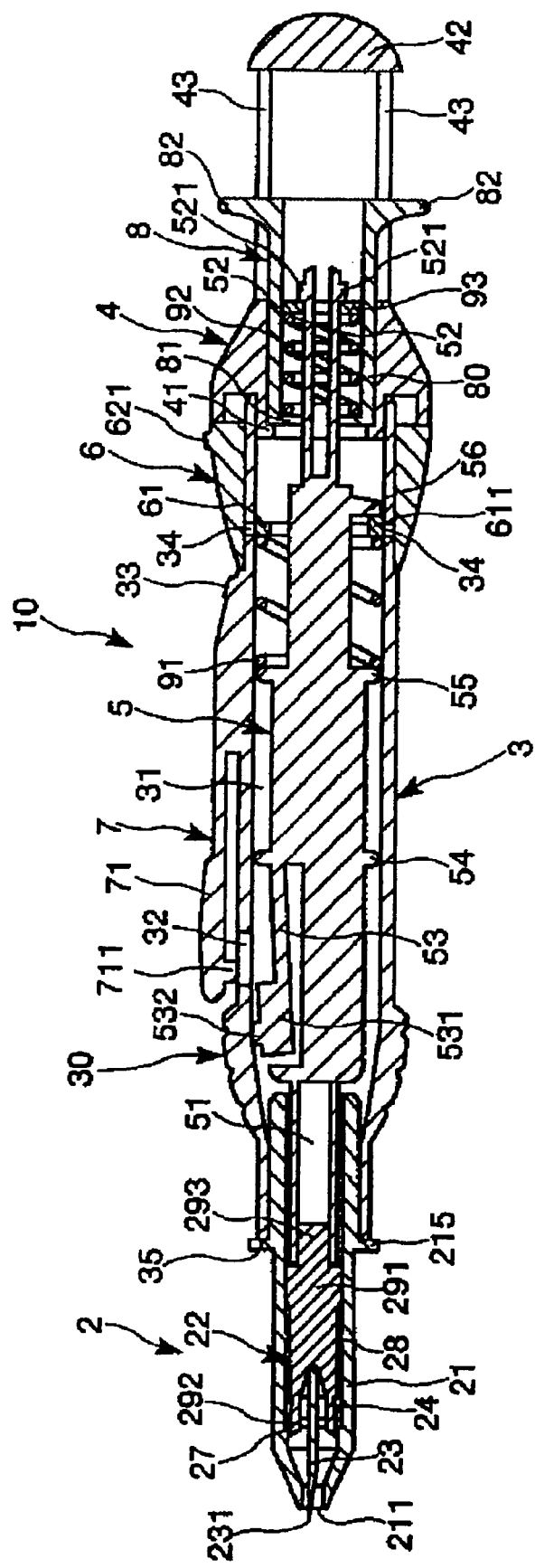
FIG. 7 is a view (longitudinal sectional view) for illustrating the method of using the lancet instrument (first embodiment) according to the invention by fitting it to the lancing apparatus.
Figure 8C:
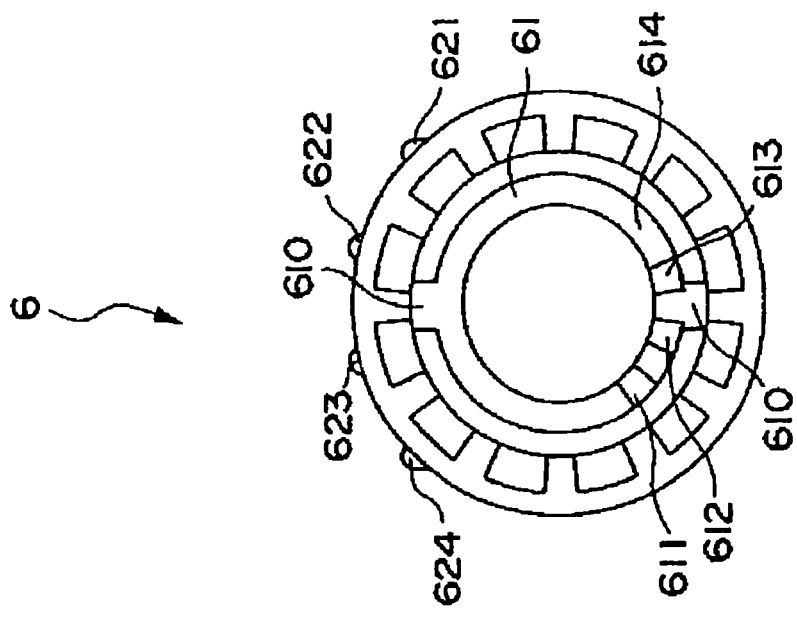
FIG. 8B is a side view of the adjusting part and FIG. 8C is an opposite end view of the adjusting part.
Figure 8B:
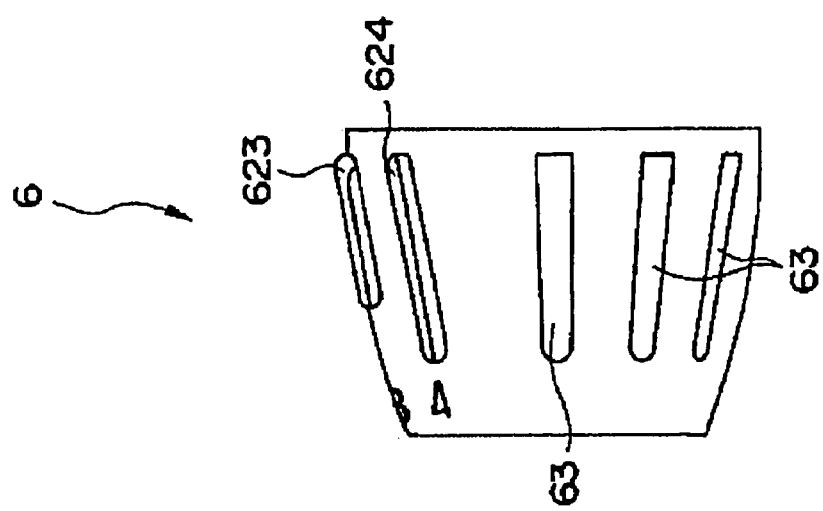
Figure 8A:
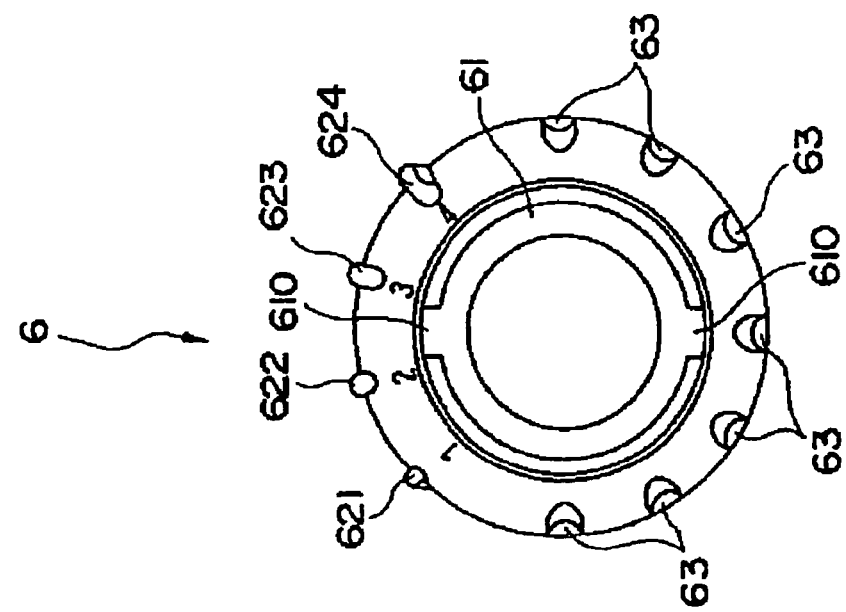
FIG. 8A is one end view of an adjusting part provided in the lancing apparatus shown in FIGS. 6 and 7.

FIGS. 1 to 5 are longitudinal sectional views showing a first embodiment of the lancet instrument according to the present invention, FIGS. 6 and 7 are views (longitudinal views) for illustrating the method of using the lancet instrument (first embodiment) according to the invention by fitting it to a lancing apparatus, and FIGS. 8A and 8C are end views and FIG. 8B is a side view showing the configuration of an adjusting part provided in the lancing apparatus shown in FIGS. 6 and 7. Incidentally, hereinafter, description will be made by referring to the left side in FIGS. 1 to 7 as "the tip", and the right side as "the base end".

A lancet instrument 2 shown in FIGS. 1 to 5 is used in the state of being detachably fitted to a lancing apparatus 10 as shown in FIGS. 6 and 7. The lancet instrument 10 has an elongate housing 3, a plunger 5, an adjusting part 6, a lancing operating part (operating means) 7, a set operating part (operating part) 8, a coil spring 91 biasing the plunger 5 in the tip direction, and a coil spring 92 biasing the plunger 5 in the base end direction.

Figures 1A, 1B:
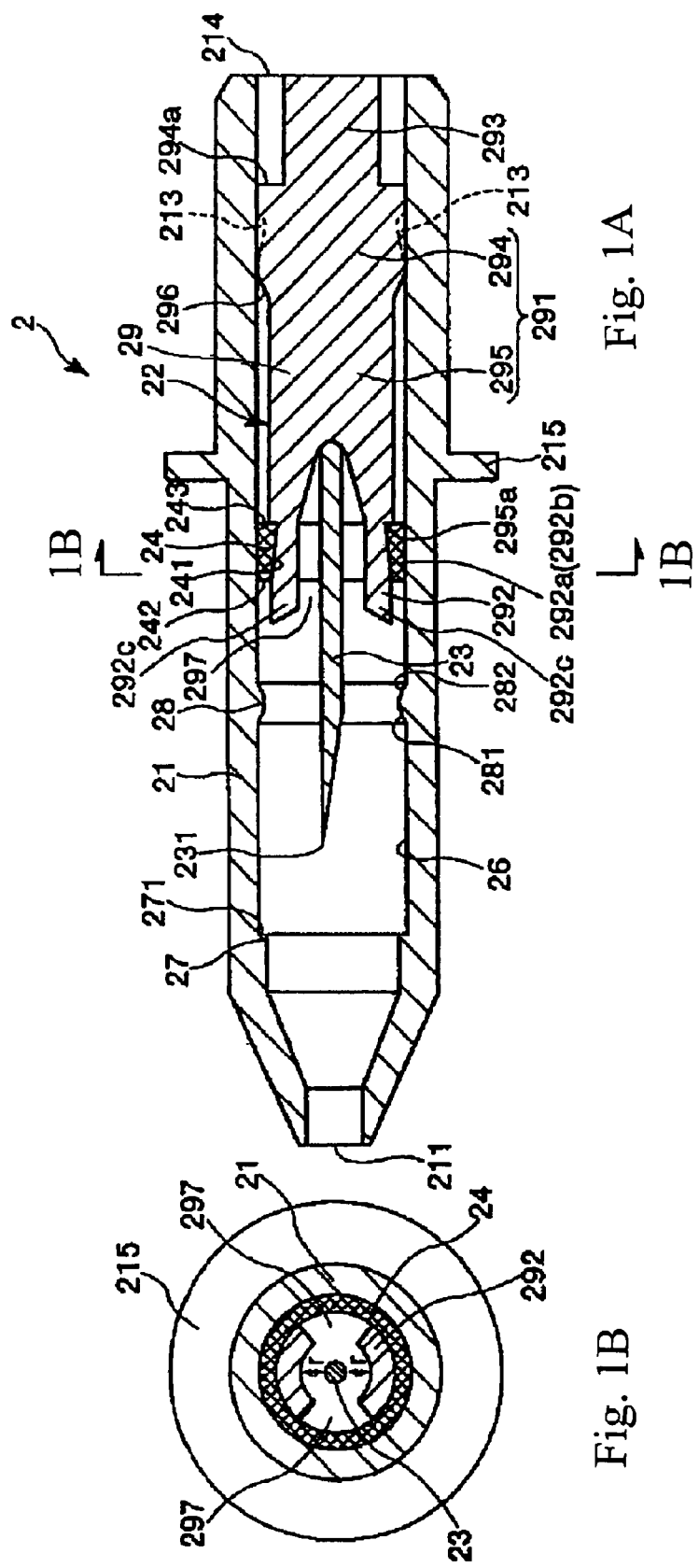
FIG. 1A is a longitudinal sectional view of a first embodiment (in a first condition) of the lancet instrument according to the present invention.
FIG. 1B is a cross sectional view of the lancet instrument along sectional line 1B-1B in FIG. 1A.
Figure 2:
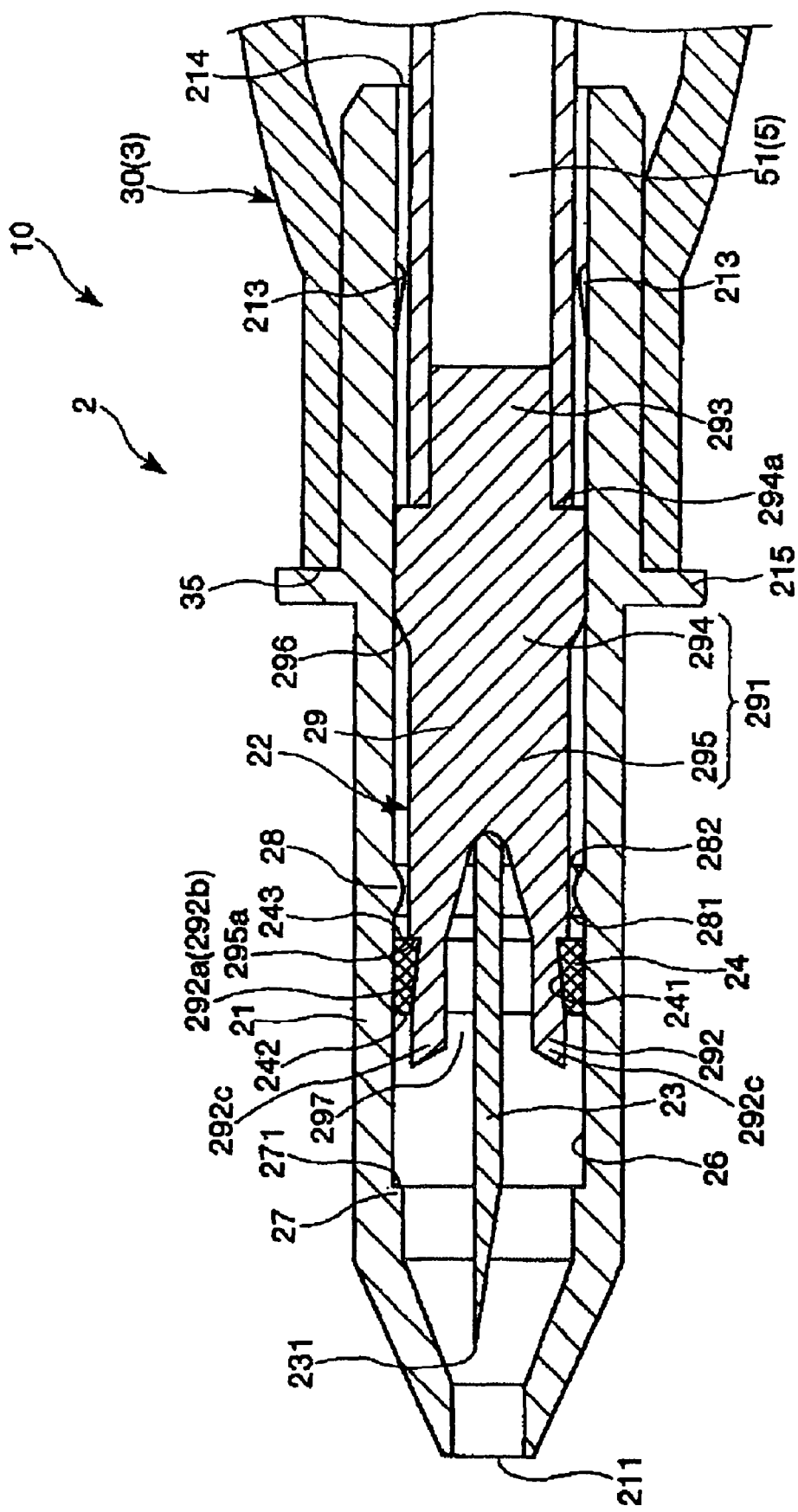
FIG. 2 is a longitudinal sectional view showing the first embodiment of the lancet instrument according to the invention.

The lancet instrument 2 shown in FIG. 1A (also in FIGS. 2 to 5) has a tubular casing (lancet holder) 21, a lancet 22 stored in the casing 21 so as to be movable in the axial direction (longitudinal direction), and a ring-like member 24 fitted over the outer periphery of the lancet 22 (an elastic deformation part 292).

As shown in FIG. 1A, the lancet 22 has a lancet body 23, and a lancet hub (hereinafter referred to simply as "the hub") 29.

The lancet body 23 is provided with a sharp lancet tip 231 at its tip.

The hub 29 has a columnar hub body 291, the elastic deformation part 292 provided on the tip side of the hub body 291 and extended in the tip direction, and a fitted part 293 provided on the base end side of the hub body 291 and fitted to the plunger 5 of the lancing apparatus 10.

The hub body 291 is fixed to a base end part of the lancet body 23 so that the lancet tip 231 of the lancet body 23 is exposed. The hub body 291 includes a large diameter part 294, and a small diameter part 295 formed on the tip side of the large diameter part 294.

The large diameter part 294 has an outside diameter approximately equal to the inside diameter of the inner peripheral part 26 of the casing 21. In addition, the large diameter part 294 is so formed that the outside diameter on the tip side thereof gradually decreases in the tip direction, i.e., it has a tapered surface 296 on the tip side.

The small diameter part 295 is formed to have an outside diameter slightly smaller than the outside diameter of the large diameter part 294. In addition, the tip side (lancet tip 231) of the lancet body 23 is exposed from the tip part of the small diameter part 295.

At the tip face 295a of the small diameter part 295, the elastic deformation part 292 is formed to project (extend) in the tip direction.

The fitted part 293 is formed to project from the base end face 294a of the large diameter part 294 of the hub body 291. Further, the fitted part 293 is formed smaller than an outside diameter of the large diameter part 294.

Incidentally, the material forming the hub 29 is not limited particularly, however; for example, various metallic materials, various plastics and the like can be used either singly or in combination.

The elastic deformation part 292 is tubular in shape, and is provided with a pair of cutouts (lost portions) 297 along the longitudinal direction thereof. The elastic deformation part 292 is composed of two projected parts 292c which are arcuate in cross sectional shape and spaced from each other. This permits easier elastic deformation of the elastic deformation part 292.

In addition, the outer periphery 292a of a fitted part 292b of the elastic deformation part 292 has a tapered shape such that the outside diameter gradually increases in the tip direction.

The elastic deformation part 292 as just-mentioned can be elastically deformed so that the distance thereof from the lancet body 23 is changed, i.e., so that the position thereof in the radial direction (the direction denoted by r in FIG. 1B) is changed. In other words, the elastic deformation part 292 can be elastically deformed into a radially contracted state where the distance thereof from the lancet body 23 is small (refer to the elastic deformation part 292 indicated by broken line (two-dotted chain line) in FIG. 4) and a radially enlarged state where the distance thereof from the lancet body 23 is large (natural state (see FIG. 5)).

Incidentally, the material forming the elastic deformation part 292 is not particularly limited; for example, the materials mentioned above in relation to the hub 29 can be used.

In the preferred embodiment (carrying-out mode) of the present invention, the ring-like member 24 is fitted over the fitted part 292b (outer periphery 292a) of the elastic deformation part 292 in the natural state. Here, the "natural state" means the condition where no external force is exerted on the elastic deformation part 292.

As shown in FIG. 1A, the ring-like member 24 has an outside diameter approximately equal to the inside diameter of the inner peripheral part 26 of the casing 21.

The inner periphery 241 of the ring-like member 24 has a tapered shape such that the diameter (inside diameter) gradually increases in the tip direction. In other words, the material thickness (thickness) on the tip side of the ring-like member 24 is smaller than the material thickness (thickness) on the base end side.

Since the inner periphery 241 of the ring-like member 24 and the outer periphery 292a of the elastic deformation part 292 have the tapered shapes, upon the release of the ring-like member 24 from the elastic deformation part 292, the elastic deformation part 292 is in the natural state, or the radially enlarged state, and its outside diameter in this instance is greater than the inside diameter on the base end side of the ring-like member 24. This prevents the ring-like member 24 from being again fitted onto the elastic deformation part 292. Namely, the ring-like member 24 is so configured as to be irreversibly released from the elastic deformation part 292.

Furthermore, since the elastic deformation part 292 is in the natural state under the condition where the ring-like member 24 is fitted, it would not be plastically deformed, and stable performance can be obtained.

It is to be noted here, however, that in the case where the elastic deformation part 292 is not plastically deformed or its plastic deformation is in a usable extent, a configuration may be adopted in which even where the inner periphery 241 of the ring-like member 24 and the outer periphery 292a of the elastic deformation part 292 are not tapered, the ring-like member 24 is fitted so as to apply a stress to the elastic deformation part 292 and put the latter into the radially contracted state, and, when the ring-like member 24 is released in the tip direction, the elastic deformation part 292 is brought into the radially enlarged state.

Incidentally, the magnitude of the taper angle of the inner periphery 241 of the ring-like member 24 (the angle indicated by θ in FIG. 5) is not particularly limited, but the taper angle is, for example, preferably in the range of 1 to 45 degrees, more preferably 3 to 15 degrees.

This provides easier release of the ring-like member 24 from the elastic deformation part 292, and makes it possible to securely prevent the released ring-like member 24 from being again fitted to the elastic deformation part 292.

As for the shape of the ring-like member 24, the outer peripheral shape is not particularly limited, insofar as it permits the ring-like member 24 to be moved along the longitudinal direction inside the casing 21. Preferably, however, the outer peripheral shape of the ring-like member 24 substantially coincides with the shape of the inner peripheral surface (inner peripheral part 26) of the casing 21, and a circular shape is more preferable because it permits easy movement of the ring-like member 24 in the longitudinal direction.

The inner peripheral shape of the ring-like member 24 is not particularly limited, insofar as it is suitable for fitting the ring-like member 24 to the elastic deformation part 292 at the time of manufacture and for releasing the ring-like member 24 at the time of use; however, a circular shape is particularly preferable.

In addition, the material forming the ring-like member 24 is not particularly limited; for example, the materials mentioned above in the description of the hub 29 can be used.

As shown in FIG. 1A, the tip of the casing 21 is a portion brought into contact with a living body surface such as, for example, fingertip, palm, arm, abdomen, thigh, ear lobe, etc., and is provided with an opening (tip opening) 211. In addition, the casing 21 is provided at its base end with an opening (base end opening) 214.

An inner peripheral part 26 of the casing 21 is provided with a ring-like member contact part 27, a lock part 28, and a hub engaging part 213.

The ring-like member contact part 27 is so formed that a tip part of the inner peripheral part 26 is reduced in inside diameter. As shown in FIG. 5, the tip face 242 of the ring-like member 24 released from the hub 29 (elastic deformation part 292) of the lancet 22 is brought into contact with the base end face 271 of the ring-like member contact part 27. This inhibits (restricts) the movement of the ring-like member 24 in the tip direction beyond the ring-like member contact parts 27.

The lock part 28 is so formed that a central part of the inner peripheral part 26 is reduced in inside diameter. Besides, slant surfaces 281 and 282 are formed respectively on the tip side and the base end side of the locking part 28.

As shown in FIG. 4, at the time of detaching the lancet instrument 2 from the lancing apparatus 10, first, the casing 21 is moved in the tip direction, so that the lancet 22 fitted to a lancet instrument fitting part 51 is relatively moved in the base end direction, and the base end face 243 of the ring-like member 24 fitted to the elastic deformation part 292 is brought into contact (engagement) with the slant surface 281 of the lock part 28. This inhibits (restricts) the movement of the ring-like member 24 in the base end direction beyond the lock part 28.

With such a lock part 28 provided, at the time of detaching the lancet instrument 2 from the lancing apparatus 10, the movement of the ring-like member 24 in the base end direction is inhibited, so that the ring-like member 24 can be assuredly released from the lancet 22 (elastic deformation part 292) pulled in the base end direction together with the lancing apparatus 10 (see FIG. 4).

In addition, the inner peripheral part 26 of the casing 21 is provided with the hub engaging part 213 which can be engaged with the outer periphery of the large diameter part 294 (hub 29). As shown in FIG. 1A, with the large diameter part 294 engaged with (locked by) the hub engaging part 213, the release of the lancet 22 from the base end side of the casing 21 can be inhibited.

Besides, the casing 21 is provided at its outer peripheral part with a ring-like rib 215 which is brought into contact with the tip 35 of the housing 3 (housing body 30) when the lancet instrument 2 is fitted to the lancing apparatus 10.

In addition, as the material forming the casing 21, various plastic materials (resin materials) can be used.

The lancet instrument 2 configured as above can assume three different states (a first state (see FIG. 1A), a second state (see FIG. 3) and a third state (see FIG. 5)).

As shown in FIG. 1A, in the first state (unused state), the ring-like member 24 is fitted to the elastic deformation part 292 of the lancet 22. The lancet 22 has its large diameter part 294 locked by the hub engaging part 213 of the casing 21, i.e., it is held in the casing 21.

In addition, the lancet tip 231 of the lancet 22 is located in the casing 21. This ensures that unwilling puncture with the lancet 22 (lancet tip 231) of the lancet instrument 2 in the unused state is prevented from occurring. Namely, safety of the lancet instrument 2 in the unused state can be maintained.

Figure 3:
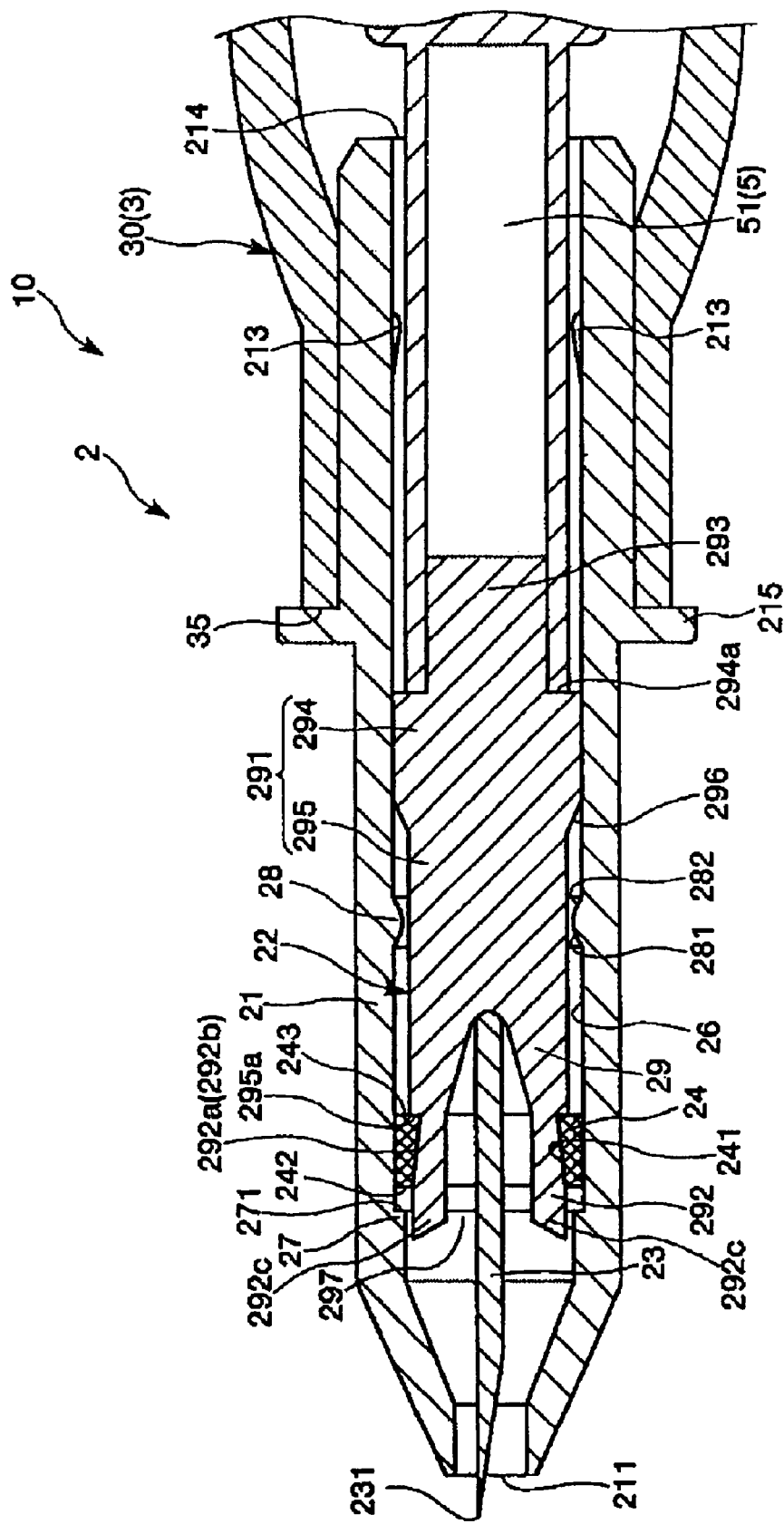
FIG. 3 is a longitudinal sectional view showing the first embodiment (in a second condition) of the lancet instrument according to the invention.

As shown in FIG. 3, in the second state (puncture state), of the lancet instrument 2 fitted to the lancing apparatus 10, the lancet 22 is moved (pushed) in the tip direction by operating the plunger 5 of the lancing apparatus 10, so as to project the lancet tip 231 through the opening 211 of the casing 21. A living body surface is punctured by the lancet tip 231 thus projected.

Incidentally, the projection amount (puncture depth) of the lancet tip 231 is set by adjusting the adjusting part 6 of the lancing apparatus 10 which will be described later. Besides, the maximum projection amount (maximum projection length) of the lancet tip 231 is restricted by the contact of the tip face 242 of the ring-like member 24 fitted to the elastic deformation part 292 with the base end face 271 of the ring-like member contact part 27.

As shown in FIG. 5, in the third state (used state), the ring-like member 24 has been released in the tip direction from the elastic deformation part 292. The ring-like member 24 thus released can enter between the ring-like member contact part 27 and the lock part 28 (the tip of the elastic deformation part 292) inside the casing 21 and move in the axial direction therebetween, so that the ring-like member 24 can be brought into contact with (be locked by) the ring-like member contact part 27. The base end face 243 of the locked ring-like member 24 is contacted by the tip of the elastic deformation part 292 being in the radially enlarged state, or natural state. This makes it possible to limit the movement of the lancet 22 in the tip direction, so that the lancet tip 231 after puncture (after use) is securely inhibited (prevented) from projecting through the opening 211 of the casing 21.

As shown in FIG. 6 (also in FIG. 7), the housing 3 possessed by the lancing apparatus 10 includes a housing body 30, and a cap-like member 4 provided at a base end part of the housing body 30. The housing 30 functions also as a grip part at the time of using the lancing apparatus 10.

The housing 3 has a hollow part 31 opened at the tip thereof, and a lancing mechanism including the plunger 5, the coil spring 91 urging the plunger 5 in the tip direction, and the coil spring 92 urging the plunger 5 in the base end direction is installed in the hollow part 31.

The casing 21 of the lancet instrument 2 is detachably fitted to a tip part of the housing 3. Specifically, at the time of fitting the lancet instrument 2 to the lancing apparatus 10, a base end part of the casing 21 is fitted into a tip part of the housing body 30.

In addition, on the upper side in FIG. 6 of the housing body 30, there are provided the elastically deformable plate-like lancing operating part 7, and an index 33. Incidentally, the index 33 is disposed on the base end side of the lancing operating part 7.

An operating button 71 having a projection 711 projected to the lower side in FIG. 6 is formed at a tip part of the lancing operating part 7. Besides, the housing body 30 is provided, at a position corresponding to the projection 711, with an opening 32 greater than the projection 711 and smaller than the operating button 71.

In addition, the housing body 30 is provided, on the base end side of the index 33, with a pair of slots 34, 34 along the circumferential direction thereof. One slot 34 is disposed on the upper side in FIG. 6, while the other slot 34 is disposed on the lower side in FIG. 6.

The plunger 5 is disposed inside the housing 3 so as to be movable in the axial direction.

The plunger 5 has, at its tip part, the hollow-cylindrical lancet instrument fitting part 51 to which the lancet 22 of the lancet instrument 2 is detachably fitted. Specifically, at the time of fitting the lancet instrument 2 to the lancing apparatus 10, a base end part (fitted part 293) of the lancet 22 is fitted into a tip part of the lancet instrument fitting part 51.

Besides, the plunger 5 is provided at its base end part with a first projected part 56 erected toward the lower side in FIG. 6.

In addition, the plunger 5 is provided at its base end part with a pair of bar-like projected parts 52, 52 erected toward the base end side, and each projected part 52 is provided with a projection 521 at a base end part thereof. One projected part 52 is disposed on the upper side in FIG. 6, while the other projected part 52 is disposed on the lower side in FIG. 6.

Besides, the plunger 5 is provided, on the upper side in FIG. 6, with an elastically deformable bar-like lock member 53. Incidentally, the lock member 53 is disposed on the base end side of the lancet instrument fitting part 51.

The lock member 53 is provided at its tip part with a lock portion 531 having a projection 532 projected toward the upper side in FIG. 6.

In the condition where preparation (setting) for puncture as will be described later is completed, the plunger 5 is biased in the tip direction relatively to the housing 3 by the coil spring 91, and, in this condition, the projection 532 of the lock part 531 is inserted in the opening 32 of the housing body 30, whereby the lock part 531 is locked relatively to the housing 3.

In addition, the plunger 5 is provided at its outer peripheral surface with ring-like flanges 54 and 55. The flange 55 is located on the base end side relative to the flange 54.

When the plunger 5 is moved, the flanges 54 and 55 are slid on the inner peripheral surface of the housing body 30, whereby the posture of the plunger 5 is maintained.

In addition, a base-end-side part of the flange 55 functions as a spring seat with which the tip side of the coil spring 91 makes contact. The adjusting part (adjusting dial) 6 being tubular in shape is disposed at a base end part of the housing body 30 and on the tip side of the cap-like member 4 so as to be turnable in the circumferential direction of the housing body 30.

As shown in FIGS. 8A and 8C, the adjusting part 6 has a pair of support parts 610, 610 formed at the inner peripheral surface thereof. These support parts 610 are provided with a ring-like puncture depth control plate (second projected part) 61 brought into contact with the projected part 56 of the plunger 5 at the time of puncture. The pair of support parts 610, 610 are inserted respectively in the above-mentioned pair of slots 34, 34 of the housing body 30, and the puncture depth control plate 61 is located inside the housing 30.

The support parts 610, 610 are located opposite to each other, through the center of the puncture depth control plate 61 therebetween. In addition, the puncture depth control plate 61 is located at a roughly middle position in the axial direction of the adjusting part 6, concentrically with the housing body 30.

The puncture depth control plate 61 has parts which differ in the position in the axial direction of contact surface for contact with the projected part 56 of the plunger 5, whereby the puncture depth of the lancet 22 (lancet tip 231) into a living body surface (=projection amount of lancet 22 from opening 211) can be adjusted.

To be more specific, the base-end-side surface of the puncture depth control plate 61 is provided with three projected parts (spacers) 611, 612 and 613 differing in height (length in the axial direction), arrayed along the circumferential direction. These projected parts 611, 612 and 613 are disposed in this order counterclockwise in FIG. 8C, at an interval of 30°.

As for the height of the projected parts 611 to 613, the projected part 611 is the tallest, the projected part 612 is the second tallest, and the projected part 613 is the smallest. In other words, as for the position in the axial direction of the contact surface of the puncture depth control plate 61 brought into contact with the projected part 56 of the plunger 5 at the time of puncture, the position of the contact surface of the projected part 611 is most on the base end side, the position of the contact surface of the projected part 613 is most on the tip side, and the position of the contact surface of the projected part 612 is between those of the projected parts 611 and 613.

Therefore, the puncture depth of the lancet 22 into a living body surface is the shallowest (smallest) when the projected part 611 faces the projected part 56 of the plunger 5, and then the puncture depth of the lancet 22 becomes deeper (greater) in the order of the projected part 612, the projected part 613, and a part 614 without any projected part.

The adjusting part 6, the plunger 5 and the projected part 56 constitute an adjusting mechanism, by which the projection amount of the lancet 22, i.e., the puncture depth into a living body surface can be adjusted according to the individual differences among the patients (testees) and the location of puncture.

A base-end-side part of the puncture depth control plate 61 functions as a spring seat with which the base end side of the coil spring 91 makes contact. When the lancet instrument 2 is not fitted to the puncture apparatus 10, the coil 91 is inserted in a substantially no-load condition (natural length) between the puncture depth control plate 61 and the above-mentioned flange 55.

In addition, the outer peripheral surface of the adjusting part 6 is provided with four ribs 621, 622, 623 and 624 differing in length.

These ribs 621, 622, 623 and 624 are disposed in the order of the ribs 621, 622, 623 and 624 counterclockwise in the right-side figure in FIG. 8C at an interval of 30° (an angular interval equal to that of the projected parts 611, 612 and 613).

Specifically, the rib 621 is located at a position shifted from the projected part 611 by 180° along the circumferential direction. In other words, the rib 621 is so disposed as to be located at the position of the index 33 when the projected part 611 faces the projected part 56 of the plunger 5.

Similarly, the ribs 622, 623 and 624 are located at positions shifted by 180° along the circumferential direction from the projected part 612, the projected part 613 and the part 614 without any projected part, respectively. In other words, the ribs 622, 623 and 624 are so disposed as to be located at the position of the index 33 when the projected part 612, the projected part 613 and the part 614 without any projected part face the projected part 56 of the plunger 5, respectively.

As for the length of the ribs 621 to 624, the rib 624 is the longest, the rib 623 is the second longest, the rib 622 is the third longest, and the rib 621 is the shortest. The length of rib indicates the level of the puncture depth of the lancet 22. Namely, as the length of rib is larger, the puncture depth of the lancet 23 into a living body surface is deeper.

In addition, numerals "1", "2", "3" and "4" indicating the levels of the puncture depth of the lancet 23 into a living body surface are provided respectively on the tip side of the ribs 621, 622, 623 and 624 on the outer peripheral surface of the adjusting part 6.

Besides, the outer peripheral surface of the adjusting part 6 is provided with a plurality of grooves 63 arrayed along the circumferential direction thereof. The grooves 63 and the ribs 621 to 624 function as nonslip section at the time of rotatingly operating the adjusting part 6.

As shown in FIG. 6, the set operating part 8 is disposed inside the cap-like member 4 so as to be movable in the axial direction.

The cap-like member 4 is provided at its tip with a ring-like rib 41 with which the tip of the set operating part 8 makes contact.

In addition, the cap-like member 4 is provided at its base end with a head part (position restricting means) 42. At the time of operating the set operating part 8, the base end of the set operating part 8 is brought into contact with the head part 42, whereby the set operating part 8 is inhibited from moving in the base end direction.

Besides, the cap-like member 4 is provided with slots 43 respectively on the upper side and on the lower side in FIG. 6.

The set operating part 8 has a hollow-cylindrical set operating part body 80 for storing the coil spring 92 therein.

The set operating part body 80 is provided with a ring-like rib 81 at its tip. A base-end-side part of the rib 81 functions as a spring seat with which the tip side of the coil spring 92 makes contact.

In addition, grip parts 82 inserted in the corresponding slots 43 of the cap-like member 4 are formed respectively on the upper side and the lower side in FIG. 6 of a base end part of the set operating part body 80. The grip part 82 on the upper side in FIG. 6 projects through the slot 43 toward the upper side (outer side) in FIG. 6, while the grip part 82 on the lower side in FIG. 6 projects through the slot 43 toward the lower side (outer side) in FIG. 6.

Besides, a ring-like spring retaining member 93 having a spring seat on the tip side thereof is disposed inside the set operating part 8 so as to be movable in the axial direction.

When the lancet instrument 2 is not fitted to the lancing apparatus 10, the coil spring 92 is inserted in a substantially no-load condition (natural length) between the spring retaining member 93 and the rib 81. The coil spring 92 is located on the base end side relative to the coil spring 91. Besides, the spring constant of the coil spring 92 is smaller than the spring constant of the coil spring 91.

The spring retaining member 93 is locked by the pair of projections 521, 521 in the condition where the pair of projected parts 52, 52 of the plunger 5 are inserted.

The conditions such as the spring constants, the axial lengths, etc. of the coil springs 91 and 92 are configured so that puncture can be performed assuredly, i.e., so that at the time of puncture the lancet 22 is securely projected through the opening 211 of the casing 21 by a predetermined amount and, thereafter, the lancet 22 is assuredly stored into the casing 21.

Now, the procedure, and the operations of the various parts, in the case of performing puncture of a living body surface by fitting the lancet instrument 2 to the lancing apparatus 10 will be described below.

[1] First, the lancet instrument 2 in the first state is fitted to the tip part of the lancing apparatus 10. Specifically, a base end part of the casing 21 is fitted into a tip part 35 of the housing 3 until the rib 215 of the casing 21 makes contact with the tip 35 of the housing 3, and a base end part of the lancet 22 is inserted into a tip part of the lancet instrument fitting part 51 of the plunger 5 (see, for example, FIG. 2).

In this case, since the large diameter part 294 of the lancet 22 is being locked by the hub engaging part 213 of the casing 21 as above-mentioned, the lancet 22 would not be moved in the tip direction unless a force of not less than a predetermined value is exerted thereon, and the flange 55 of the plunger 5 is in contact with the tip of the coil spring 91.

The force for moving the large diameter part 294 of the lancet 22 from the hub engaging part 213 is configured to be greater than the forces for compressing the coil springs 91, 92. This setting ensures that by the operation of fitting the base end part of the lancet 22 into the tip part of the lancet instrument fitting part 51 of the plunger 5, the plunger 5 can be simultaneously moved in the base end direction against the elastic forces of the coil springs 91, 92, and the projection 532 in the lock part 531 of the locking member 53 of the plunger 5 is inserted into the opening 32 of the housing 3, whereby the preparation (setting) for puncture is completed. Further, by pushing the lancet 22 in the base end direction, the large diameter part 294 of the lancet 22 is moved from the hub engaging part 213, and is released from the engagement with the hub engaging part 213. The lancet instrument 2 is stopped by the contact of the base end side surface of the rib (flange) 215 with the tip 35 of the housing body 30.

This ensures that the fitted part 293 of the lancet 22 can be assuredly (easily) fitted into the lancet instrument fitting part 51 of the plunger 5. In addition, the preparation for puncture can be carried out easily, quickly and assuredly.

In addition, by the operation of fitting the lancet instrument 2 to the lancing apparatus 10, the ring-like member 24 fitted to the elastic deformation part 292 is made to ride over the lock part 28 from the base end side to the tip side, to be located between the ring-like member contact part 27 and the lock part 28. The contact between the base end face 243 of the ring-like member 24 and the tip face 295a of the hub body 291 is performed substantially perpendicularly to the moving direction of the lancet 22, so that the ring-like member 24 would not be released to the base end side upon riding over the lock part 28.

The angle of contact of the base end face 243 of the ring-like member 24 with the hub 29 is preferably 70 to 150 degrees, more preferably 90 to 120 degrees, from the tip end direction of the lancet 22.

Incidentally, in the lancing apparatus 10 in the condition where the lancet instrument 2 is not fitted thereto, the lock member 53 of the plunger 5 is displaced (elastically deformed) toward the right side in FIG. 6, due to the contact of the projection 532 of the lock part 531 with the inner peripheral surface of the housing 3. In other words, the lock part 531 is urged toward the upper side in FIG. 6 by the elastic force of the lock member 53.

[2] If necessary, the puncture depth of the lancet 22 (lancet tip 231) into the living body surface is adjusted. Specifically, the puncture depth of the lancet 22 into the living body surface is set to a puncture depth according to the individual difference of the person from whom blood is to be sampled, and to the location of puncture.

As a reference in setting the puncture depth, for example, a puncture depth at which the required minimum blood amount for blood sugar measurement is obtained may be adopted. This makes it possible to minimize the pain at the time of puncture.

In the case of setting the puncture depth, the adjusting part 6 is gripped with fingers, and the adjusting part 6 is rotated in the circumferential direction relatively to the housing 3, so as to locate a predetermined one of the ribs 621 to 624 at the position of the index 33.

The setting of the puncture depth, once conducted, need not be repeated each time of blood sampling; therefore, the operation does not take time and labor.

Incidentally, FIGS. 6 and 7 each show the condition where the puncture depth of the lancet 22 into the living body surface is at the minimum level.

[3] After the tip of the casing 21 of the lancet instrument 2 is pressed against a predetermined location, for example, a living body surface such as a fingertip, the operating button 71 of the puncture operating part 7 is depressed (pushed to the lower side in FIG. 6).

With the operating button 71 depressed, as shown in FIG. 7, the projection 711 thereof pushes the projection 532 of the lock part 531, whereby the lock member 53 is elastically deformed, and the lock part 531 is displaced downward in FIG. 7, and the lock of an edge part, fronting on the opening 32, of the projection 532 of the lock part 531 is released (unlocked).

On the other hand, the puncture operating part 7 is elastically deformed, and, when the finger is released from the operating button 71, the puncture operating part 7 having been elastically deformed returns into its original shape by its elastic force.

When the lock of the lock part 531 is released, as shown in FIG. 7 (FIG. 3), the coil spring 91 having been compressed extends by its elastic force, whereby the plunger 5 is moved in the tip direction, and the lancet tip 231 of the lancet 22 is projected through the opening 211 of the casing 21, to puncture the living body surface. Namely, the lancet instrument 2 is put into the second state.

Incidentally, since the movement of the plunger 5 in the tip direction is restricted by the contact of the projected part 56 of the plunger 5 with the projected part 611 of the puncture depth control plate 61, the puncture depth of the lancet 22 into the living body surface is adjusted to a fixed value (minimum value).

In addition, during the movement of the plunger 5 in the tip direction, the coil spring 91 and the flange 55 part from each other, in the course of this movement, and the coil spring 92 is gradually compressed, so that the plunger 5 is urged by the coil spring 92 in the base end direction relatively to the housing 3.

In this case, as above-mentioned, the spring constant of the coil spring 91 is greater than the spring constant of the coil spring 92; therefore, the plunger 5 is moved toward the tip side against the elastic force of the coil spring 92, so that the living body surface can be punctured by the lancet 22.

In addition, after parting from the flange 55, the coil spring 91 returns to its natural length, so that it does not urge the plunger 5 in the tip direction or the base end direction.

After the puncture of the living body surface by the lancet 22, the coil spring 92 having been compressed extends by its elastic force, whereby the plunger 5 is moved in the base end direction, the lancet 22 is pulled out from the living body surface, and the lancet 22 is contained (stored) into the casing 21.

[4] After the puncture, the lancet instrument 1 is separated from the living body surface, and the blood on the puncture location is sampled. The blood sampling can be conducted, for example, by a method in which the blood is supplied directly onto a test paper, or is sucked through a fine tube and supplied to a test paper.

[5] Even in the case where the operating button 71 is erroneously depressed before puncture of a living body surface, the lancet 22 can be reset. The resetting is done by gripping the grip part 82 of the set operating part 8 with fingers, then moving the set operating part 8 in the base end direction relatively to the housing 3 against the elastic forces of the coil springs 91 and 92, and releasing the fingers from the grip part 82 after the base end of the set operating part 8 makes contact the head part 42 of the housing 3.

In this case, first, the coil spring 92 with the smaller spring constant is gradually compressed, then the coil spring 91 with the greater spring constant is gradually compressed, and the plunger 5 is moved in the base end direction by an amount corresponding to the compression amount of the coil spring 91.

When the set operating part 8 is moved until its base end makes contact with the head part 42 of the housing 3, the projection 532 of the lock part 531 in the lock member 53 of the plunger 5 is located on the right side of the opening 32 of the housing 3, the lock member 53 having been elastically deformed returns to its original shape by its elastic force, the projection 532 is inserted into the opening 32 of the housing 3, and the projection 532 makes contact with (or faces) the projection 711 of the operating button 71 (see FIG. 6).

When the fingers are released from the grip part 82, as shown in FIG. 6, the projection 532 of the lock part 531 makes contact with a tip-side edge part fronting on the opening 32 of the housing 3, whereby the lock part 531 is locked relatively to the housing 3, and, as a result, the compressed condition of the coil spring 91, i.e., the condition where the plunger 5 is urged in the tip direction relatively to the housing 3 by the coil spring 91, is maintained.

On the other hand, when the fingers are released from the grip part 82, as shown in FIG. 6, the coil spring 92 having been compressed extends by its elastic force, whereby the set operating part 8 is moved forward the tip side until its rib 81 makes contact with the rib 41 of the housing 3. In addition, the coil spring 92 returns to its natural length, and does not urge the plunger 5 in the tip direction or the base end direction.

In this condition, the preparation (setting) for puncture of a living body surface is completed. In this way, in the lancing apparatus 10, the preparation for puncture of a living body surface can be carried out easily, speedily and assuredly.

[6] Thereafter (after use), the lancet instrument 2 is detached from the lancing apparatus 10, and is discarded. For detaching the lancet instrument 2 from the lancing apparatus 10, the casing 21 is gripped with one hand, and, in this condition, the lancing apparatus 10 is pulled in the base end direction by the other hand.

In this instance, as above-mentioned, the ring-like member 24 is moved (pulled) in the base end direction together with the lancet 22, but it is locked by the lock part 28 so as to be restrained from further movement.

Besides, the lancet 22 is moved further in the base end direction together with the lancing apparatus 10; at last, the elastic deformation part 292 is put into a radially contracted state, and the ring-like member 24 is released from the elastic deformation part 292 being in that state (see FIG. 4). Thereafter, the lancet 22 is restrained from further movement, i.e., is inhibited from release from the base end side of the casing 21, since its large diameter part 294 is locked by (engaged with) the hub engaging part 213 of the casing 21. Incidentally, the force for releasing the hub 29 from the tip part of the lancet instrument fitting part 51 is configured to be greater than the force for releasing the ring-like member 24 from the elastic deformation part 292. This ensures that the ring-like member 24 can be assuredly released from the elastic deformation part 292 before the lancet 22 is detached from the plunger 5.

By pulling the lancing apparatus 10 further in the base end direction, the lancet instrument 2 is detached from the lancing apparatus 10. Upon this, the lancet instrument 2 is put in the third state (see FIG. 5). For example, as shown in FIG. 5, even if it is tried to re-fit the used lancet instrument 2 to the lancing apparatus 10 and the plunger 5 pushes the lancet 22 in the tip direction, the elastic deformation part 292 is put in the radially enlarged state (natural state) so as to inhibit the lancet tip 231 from projecting through the opening 211.

Since the lancet tip 231 would not project through the opening 211, erroneous injuring of a skin or the like and infection can be prevented in discarding the lancet instrument 2.

Thus, the lancet instrument 2 is so configured that the ring-like member 24 is irreversibly released from the elastic deformation part 292, whereby it is ensured that the released ring-like member 24 cannot be re-fitted to the elastic deformation part 292 and that the tip of the elastic deformation part 292 is assuredly brought into contact with the base end face of the ring-like member 24. This restricts (limits) the movement of the lancet 22 in the tip direction, so that the lancet tip 231 after puncture (after use) can be securely prevented from projecting through the opening 211.

Incidentally, the application of the lancet instrument 2 according to the present invention is not limited to blood sampling as in this embodiment; for example, the lancet instrument 2 can be applied also to a system for sampling such a body fluid as interstitial fluid.

Second Embodiment

Figure 9:
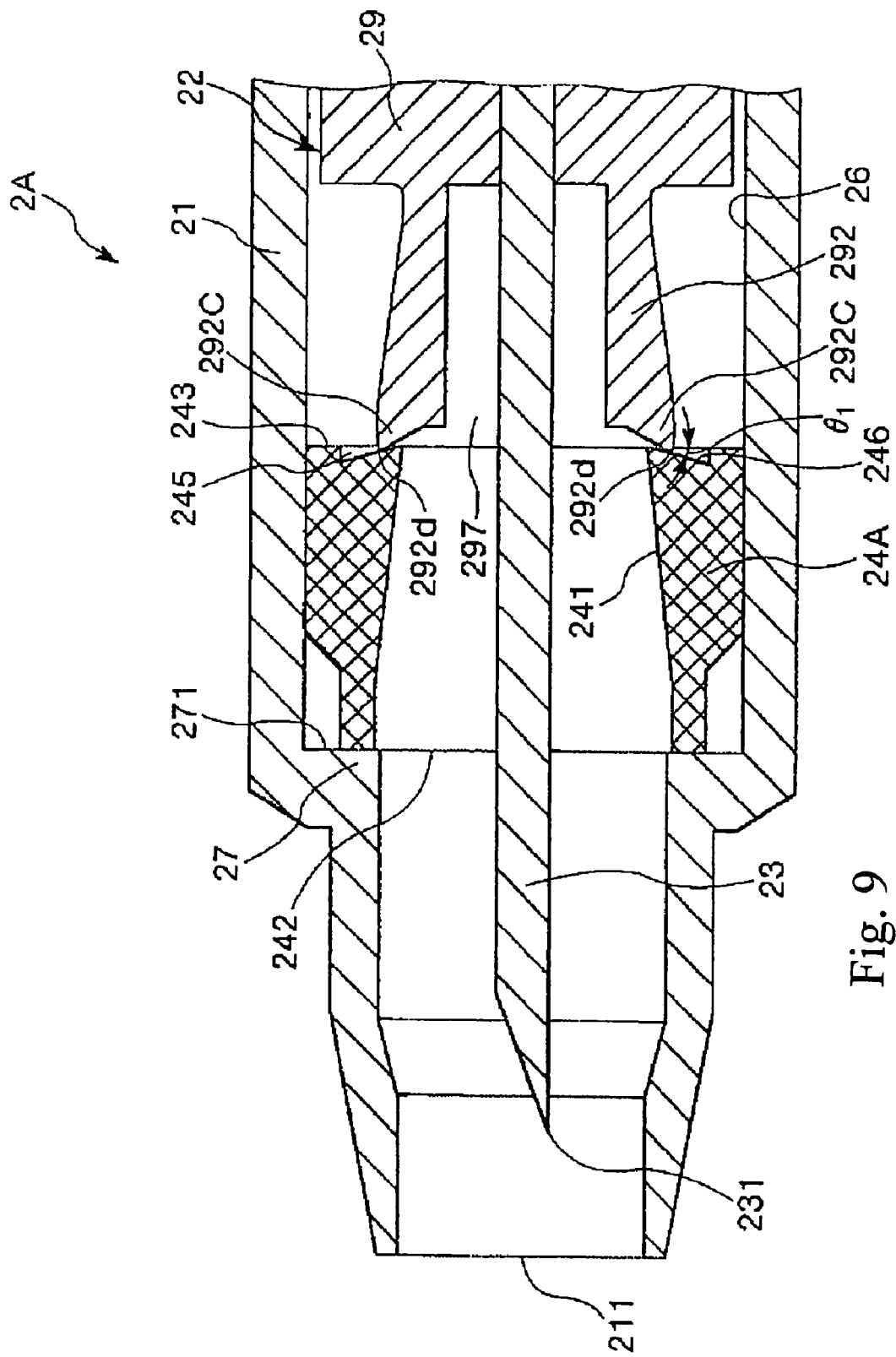
FIG. 9 is a longitudinal sectional view showing a second embodiment of the lancet instrument according to the present invention.

FIG. 9 is a longitudinal sectional view showing a second embodiment of the lancet instrument according to the present invention. Incidentally, hereinafter, the description will be made by referring to the left side in FIG. 9 as the "tip", and the right side as the "base end".

Now, referring to this figure, the second embodiment of the lancet instrument according to the present invention will be described. The following description will be focused on the differences from the above-described embodiment, and descriptions of the same items as above will be omitted.

This embodiment is the same as the first embodiment, except for the shape of the ring-like member.

As shown in FIG. 9, a ring-like member 24A of a lancet instrument 2A is provided at its base end face 243 with a ring-like recess 245 concentric with the ring-like member 24A.

The recess 245 is wedge-shaped in section, and has a slant surface (bottom surface) 246 inclined against the base end face 243, i.e., inclined so that the depth of the recess 245 gradually increases along the radial direction.

Incidentally, the magnitude of the inclination angle (the angle denoted by θ in FIG. 9) of the slant surface 246 is not particularly limited; for example, the inclination angle is preferably 5 to 30 degrees, more preferably 10 to 25 degrees.

In the lancet instrument 2A having such a ring-like member 24A, when a lancet 22 is moved in the tip direction and each tip 292d of an elastic deformation part 292 (projected parts 292c) reaches the ring-like member 24A and, further, the lancet 22 is moved in the tip direction, each tip 292d of the elastic deformation part 292 comes to be along the slant surface 246. As a result, the elastic deformation part 292 is put into a radially enlarged state, and each tip 292d of the elastic deformation part 292 is fitted in the recess 243. Therefore, a lancet tip 231 after puncture is prevented more securely from projecting through an opening 211 of a casing 21.

While the lancet instrument according to the present invention has been described above based on the embodiments thereof shown in the drawings, the invention is not limited to the embodiments, and the configuration of each part can be replaced by an arbitrary configuration having the same or equivalent function to the above-described.

In addition, the elastic deformation part is not limited to the one includes two projected parts spaced from each other; for example, it may includes three or more projected parts.

Besides, the plan-view shape of the ring-like member may, for example, an O shape, or a shape obtained by removing a part of the O shape, namely, a C shape.

INDUSTRIAL APPLICABILITY

The lancet instrument according to the present invention is a lancet instrument detachably fitted to a lancing apparatus when used, includes: a lancet having a lancet body with a sharp lancet tip at its tip, a lancet hub fixed to the lancet body so that the lancet tip is exposed, and an elastic deformation part extended from the lancet hub and elastically deformable so that the distance thereof from the lancet body can be changed; a ring-like member fitted to the outer periphery of the elastic deformation part and releasable in the tip direction by changing the distance between the elastic deformation part and the lancet body; and a casing having a ring-like member contact part storing the lancet so as to be movable in the longitudinal direction and formed in an inner peripheral part thereof so that the ring-like member is brought into contact therewith and blocked to move in the tip direction, and a tip opening through which the lancet tip can be projected, wherein the projection of the lancet tip through the tip opening of the casing is blocked by moving the ring-like member released from the elastic deformation part in the tip direction between the tip of the elastic deformation part and the ring-lie member contact part to restrict the movement of the lancet. Therefore, the movement of the lancet in the tip direction is restricted by the contact of the elastic deformation part of the lancet with the ring-like member released from the elastic deformation part, so that the lancet tip after puncture can be securely prevented from projecting through the tip opening. Accordingly, the lancet instrument of the present invention has an industrial applicability.

The invention claimed is:

1. A lancet instrument adapted to be detachably fitted to a lancing apparatus when used, comprising:
    a lancet defined by a lancet body with a sharp lancet tip at its tip and a lancet hub fixed to said lancet body so that the lancet tip is exposed, said lancet hub including an elastic deformation part that is elastically deformable so that the distance of said elastic deformation part from said lancet body can be changed;
    a ring-like member separate and distinct from said lancet, said ring-like member being fitted to an outer periphery of said elastic deformation part of said lancet hub so that a distal-most end of the ring-like member is positioned proximally of a distal-most end of the elastic deformation part of said lancet hub, the ring-like member being releasable from said elastic deformation part of said lancet hub in a tip direction by changing the distance between said elastic deformation part of said lancet hub and said lancet body, wherein, upon release of said ring like member from said elastic deformation part, said elastic deformation part expands to a radially enlarged state in order to limit movement of the lancet hub in the tip direction; and
    a casing storing said lancet so as to be movable in the longitudinal direction, the casing having a ring-like member contact part formed in an inner peripheral part of the casing so that the ring-like member is brought into contact with the ring-like member contact part and is blocked to move in the tip direction, and the casing possessing a tip opening through which said lancet tip can be projected;
    wherein the projection of said lancet tip through said tip opening of said casing is blocked by moving said ring-like member released from said lancet hub in the tip direction between the distal-most end of said elastic deformation part of said lancet hub and said ring-like member contact part to restrict the movement of said lancet;
    wherein an inner periphery of said ring-like member has a tapered shape such that an inside diameter of the ring-like member gradually increases in the tip direction; and
    wherein an outer periphery of a fitting part of said elastic deformation part, to which said ring-like member is fitted, has a tapered shape such that an outside diameter of the fitting part gradually increases in the tip direction.

2. The lancet instrument according to claim 1, wherein the tapered shape of the inner periphery of said ring-like member possesses a taper angle in the range of 1 to 45 degrees.

3. The lancet instrument according to claim 1, wherein said ring-like member is irreversibly released from said elastic deformation part.

4. The lancet instrument according to claim 1, wherein said elastic deformation part is comprised of a plurality of projected parts spaced from each other.

5. The lancet instrument according to claim 1, wherein
    said casing is provided at an inner peripheral part thereof with a lock part inhibiting the movement of said ring-like member in a base end direction; and
    said ring-like member fitted to said elastic deformation part is brought into contact with said lock part and released from said elastic deformation part by moving said lancet in the base end direction relative to said casing.

6. The lancet instrument according to claim 1, wherein
    said casing is provided at an inner peripheral part thereof with a hub engaging part in engagement with an outermost peripheral surface of said lancet hub; and
    a force for releasing said lancet hub from said hub engaging part is greater than the force for releasing said ring-like member from said elastic deformation part.

7. A lancet instrument in combination with a lancing apparatus,
    the lancet instrument comprising:
        a casing possessing a hollow interior portion communicating with an open tip end at a tip end of the casing which opens to outside the casing, the casing possessing an inner peripheral surface;
        a lancet movably positioned in the hollow interior portion of the casing, the lancet comprising a lancet hub and a lancet body possessing a distalmost sharp lancet tip, the lancet body being secured to the lancet hub so that the lancet hub and the lancet body move together;
        a ring-shaped member fitted to an outer periphery of a tip end portion of the lancet hub;
        an inwardly directed lock part provided on the inner peripheral surface of the casing;
    the lancet being movable relative to the casing from a first position in which the sharp lancet tip of the lancet body is positioned on a base end side of the open tip end of the casing so that the sharp lancet tip does not project beyond the tip end of the casing to a second position in which the sharp lancet tip of the lancet extends through the open tip end of the casing and the ring-shaped member fitted to the outer periphery of the tip end portion of the lancet hub is positioned on a tip end side of the lock part of the casing; and
    the lancet being movable relative to the casing from the second position toward a third position during which the sharp lancet tip of the lancet body is retracted into the interior of the casing so that the sharp lancet tip does not project beyond the tip end of the casing and the ring-shaped member contacts the lock part of the casing to move the ring-shaped member relative to the lancet hub toward a tip end of the lancet hub;
    wherein an inner periphery of said ring-shaped member has a tapered shape such that an inside diameter of the ring-shaped member gradually increases in a tip direction; and wherein the tip end portion of the lancet hub comprises a plurality of circumferentially spaced apart projecting parts on which the ring-shaped member is fitted, an outer periphery of a part of the projecting parts having a tapered shape such that an outside diameter of the projecting parts gradually increases in the tip direction, wherein said projecting parts expand to a radially enlarged state during movement to the third position; and the lancing apparatus comprising:
  a housing; and
  a plunger positioned in the housing and axially movable relative to the housing, the plunger possessing a distal end portion at which is located a lancet instrument fitting part, the lancet instrument fitting part engaging the lancet hub to move the lancet from the second position to the third position as the plunger is axially moved relative to the housing.

8. The lancet instrument in combination with the lancing apparatus according to claim 7, wherein the ring-shaped member is irreversibly moved off of the projecting parts of the lancet as a result of the ring-shaped member contacting the lock part while the lancet is moved from the second position towards the third position.

9. The lancet instrument in combination with the lancing apparatus according to claim 7, wherein the ring-shaped member comprises first and second ends, the first end of the ring-shaped member being closer to the tip end of the casing than the second end of the ring-shaped member, the ring-shaped member possessing an inner diameter that gradually increases towards the first end of the ring-shaped member.

10. The lancet instrument in combination with the lancing apparatus according to claim 7, wherein the inner peripheral surface of the casing possesses an inwardly extending contact part, the contact part being spaced from the lock part in a direction toward the tip end of the casing, the contact part having an inner dimension smaller than an outer dimension of the ring-shaped member.

11. The lancet instrument in combination with the lancing apparatus according to claim 10, wherein the contact part and the lock part are spaced apart by a distance greater than an axial distance between opposite ends of the ring-shaped member.

12. The lancet instrument in combination with the lancing apparatus according to claim 7, wherein the ring-shaped member is irreversibly moved off of the tip end portion of the lancet as a result of the ring-shaped member contacting the lock part while the lancet is moved from the second position towards the third position.

13. The lancet instrument in combination with the lancing apparatus according to claim 12, wherein the inner peripheral surface of the casing comprises an inwardly extending hub engaging part that engages an outer periphery of the lancet hub when the lancet is in the first position, and wherein a force required to release engagement of the lancet hub from the hub engaging part is greater than the force required to move the ring-shaped member off of the outer periphery of the tip end portion of the lancet hub.

14. A lancet instrument detachably fittable to a lancing apparatus, comprising:
  a casing possessing a hollow interior portion communicating with an open tip end at a tip end of the casing which opens to outside the casing, the casing possessing an inner peripheral surface;
  a lancet movably positioned in the hollow interior portion of the casing, the lancet comprising a lancet hub and a lancet body possessing a sharp lancet tip, the lancet body being secured to the lancet hub so that the lancet hub and the lancet body move together, the lancet hub possessing a tip end portion surrounding the lancet body and spaced radially outwardly from the lancet body;
  a ring-shaped member separate and distinct from said lancet, said ring-like member having a centrally located through opening, the ring-shaped member being fitted to an outer periphery of the tip end portion of the lancet hub so that the tip end portion of the lancet hub is positioned in the centrally located through opening in the ring-shaped member and a distal-most end of the ring-like member is positioned proximally of the tip end portion of the lancet hub;
  an inwardly directed contact part provided on the inner peripheral surface of the casing, the contact part forming an inner dimension smaller than an outer dimension of the ring-shaped member;
  the lancet being movable relative to the casing from a first position in which the sharp lancet tip of the lancet body is positioned on a base end side of the open tip end of the casing so that the sharp lancet tip does not project beyond the tip end of the casing to a second position in which the sharp lancet tip of the lancet extends through the open tip end of the casing;
  the lancet being movable relative to the casing from the second position toward a third position during which the sharp lancet tip is retracted into the interior of the casing, the ring-shaped member engages a lock part of the casing to cause the ring-shaped member to move relative to the lancet in a tip end direction, and the ring-shaped member is positioned on a base end side of the contact part; and
  the ring-shaped member contacting the contact part of the casing when the lancet, which has been moved from the second position towards the third position, is moved in the tip end direction to stop movement of the lancet and prevent the sharp lancet tip from projecting beyond the tip end of the casing;
  wherein an inner periphery of said ring-shaped member has a tapered shape such that an inside diameter of the ring-shaped member gradually increases in a tip end direction; and
  wherein the tip end portion of the lancet hub comprises a plurality of circumferentially spaced apart projecting parts on which the ring-shaped member is fitted, an outer periphery of a part of said projecting parts having a tapered shape such that an outside diameter of the projecting parts gradually increases in the tip end direction, wherein said projecting parts expand to a radially enlarged state during movement to the third position.

15. The lancet instrument according to claim 14, further comprising an inwardly directed lock part on the inner peripheral surface of the casing, the lock part and the contact part being spaced apart from one another along a longitudinal extent of the casing, the lock part possessing an inner dimension smaller than an outer dimension of the ring-shaped member so that as the lancet is moved from the second position towards the third position, the ring-shaped member contacts the lock part and causes the ring-shaped member to be irreversibly moved off of the tip end portion of the lancet hub.

16. The lancet instrument according to claim 15, wherein the contact part and the lock part are spaced apart by a distance greater than an axial distance between opposite ends of the ring-shaped member.

17. The lancet instrument according to claim 14, wherein the inner peripheral surface of the casing comprises an inwardly extending hub engaging part that engages an outer periphery of the lancet hub when the lancet is in the first position, and wherein a force required to release engagement of the lancet hub from the hub engaging part is greater than the force required to move the ring-shaped member off of the outer periphery of the tip end portion of the lancet hub.

18. The lancet instrument according to claim 1, wherein the ring-like member is positioned between a radially inwardly facing inner cylindrical surface of the casing and the outer periphery of the elastic deformation portion which faces radially outwardly so that an inner surface of the ring-like member faces the outer periphery of the elastic deformation portion, and an outer surface of the ring-like member faces the radially inwardly facing inner cylindrical surface of the casing.

19. The lancet instrument according to claim 7, wherein the lancet hub possesses a tip end extending beyond the tip end of the ring-shaped member, in the tip end direction, in the first position.

20. The lancet instrument according to claim 7, wherein the ring-shaped member possesses a tip end and a base end, and wherein the lancet is movable relative to the casing from the first position to the second position in which the ring-shaped member fitted to the outer periphery of the tip end portion of the lancet hub is positioned so that the base end of the ring-shaped member is on a tip end side of the lock part of the casing.

21. The lancet instrument according to claim 14, wherein the ring-shaped member possesses a tip end positioned on the base end side of the tip end of the lancet hub.

* * * * *